United States Patent [19]
Collins et al.

[11] Patent Number: 5,485,099
[45] Date of Patent: Jan. 16, 1996

[54] SENSING METHOD AND DEVICE

[75] Inventors: Brian Collins, Chalfont St. Giles; Michael J. Blanchard, Chesham, both of United Kingdom

[73] Assignee: Blanchard Marketing Services Limited, Buckinghamshire, United Kingdom

[21] Appl. No.: 854,652

[22] PCT Filed: Sep. 20, 1990

[86] PCT No.: PCT/GB90/01456

§ 371 Date: May 14, 1992

§ 102(e) Date: May 14, 1992

[87] PCT Pub. No.: WO91/04486

PCT Pub. Date: Apr. 4, 1991

[30] Foreign Application Priority Data

Sep. 22, 1989 [GB] United Kingdom ............... 8921413
Feb. 7, 1990 [GB] United Kingdom ............... 9002664
Mar. 6, 1990 [GB] United Kingdom ............... 9004974
Jul. 12, 1990 [GB] United Kingdom ............... 9015384

[51] Int. Cl.⁶ ............................................. G01R 29/26
[52] U.S. Cl. ........................ 324/439; 324/693; 162/198
[58] Field of Search ........................ 324/713, 439, 324/693, 691, 444; 162/160.4, 198, 183, DIG. 10

[56] References Cited

U.S. PATENT DOCUMENTS

| | | | |
|---|---|---|---|
| 3,566,233 | 2/1971 | Kahn | 324/715 |
| 3,622,448 | 11/1971 | Adams | 162/198 |
| 3,649,444 | 3/1972 | Futch, Jr. | 162/198 |
| 3,687,802 | 8/1972 | Rummel et al. | 162/198 |
| 3,692,624 | 9/1972 | Yrjala | 162/49 |
| 3,859,163 | 1/1975 | Haythornthwaite | 162/198 |
| 3,904,365 | 9/1975 | Larson et al. | 324/439 |
| 4,546,318 | 10/1985 | Bowden | 324/715 |

FOREIGN PATENT DOCUMENTS

| | | |
|---|---|---|
| 0259820 | 3/1988 | European Pat. Off. . |
| 3838139 | 6/1989 | Germany . |
| 560899 | 4/1975 | Switzerland . |

OTHER PUBLICATIONS

Strazdins; Pulp and Paper Mar. 1984. Chemical Aids Can Offset Strength Loss in Secondary Fiber Use.
Koethe et al.; Surface Charge vol. 76, No. 12 Tappi Journal, Polyelectrolyte Interactions with Papermaking Fibers.
Derwent's Abstract No. 557 82 K/23, SU 945 268, publ. week 8323.
"Getting YOur Money's Worth from Filtration", Logsdon and Fox, Journal AWWA Research and Technology, May 1982.

*Primary Examiner*—Maura K. Regan
*Attorney, Agent, or Firm*—Dann, Dorfman, Herrell and Skillman; Henry H. Skillman

[57] ABSTRACT

Devices and methods for sensing the charge condition of a mixed stream of aggregant and aqueous dispersion of charged particles are based on sensing changes in the potential of an electrode contacting the stream. Sensing the changes in potential permits better control of aggregation in raw water and effluent treatments.

19 Claims, 4 Drawing Sheets

SENSING METHOD AND DEVICE

This invention is concerned with a method of following the influence of a coagulant and/or flocculant (hereafter referred to as an "aggregant") on a stream of an aqueous dispersion of charged solid or liquid particles and a device suitable as one component of a control loop process governing dosing of the aggregant.

THE FIELD OF THE INVENTION

The process of aggregating aqueous dispersions of charged particles is widespread in many industries, including, for example, the treatment of raw water in making drinking water, effluent and sludge treatment and paper-making.

The stability of an aqueous dispersion depends on the electrical double layers which exist at the surfaces of the particles and extend into the liquid phase. Coagulation is caused by changes in the structure of the double layers.

The most widely used method of coagulating a disperse system, is to add colloids having an effective change opposite in sign to that carried at the surface of the disperse phase: thus "solutions" of alum or ferric salts (in fact dispersions of colloidal cationic hydroxylic polymers of aluminum or of ferric iron) are effective coagulating agents for natural dispersions such as raw water, sludge and effluent and some man-made dispersions such as pulp dispersions used in paper-making, all of which are anionic.

Maintaining ideal coagulation conditions in a stream has never been easy. The jaw test which is in widespread use is at best an uncertain guide; the process is so lengthy that by the time the result is available, the condition of the stream may have changed so significantly that the test is no longer appropriate to determine the action to be taken.

Flocculation involves the interaction of a colloidal solution of a flocculant with the disperse phase.

DISCUSSION OF THE PRIOR ART

The first, and hitherto the only, step towards automating the maintenance of a chosen aggregation condition in a mixed stream of an aqueous dispersion and an aggregant, was to use devices utilising the electrokinetic phenomenon of streaming current. An account of the competence of these devices generally known as Streaming Current Detectors, or SCDs, is contained in the specification of European Patent Application 88901621.8 SCDs have a shared essential characteristic, namely that samples of the stream are caused to flow back and fore through a capillary, limiting the in-line application of SCDs to monitoring the treatment of very dilute dispersions of colloids of small particle size, like some raw waters in making drinking water. The range of applications of SCDs was increased by the discovery that the charged condition of the filtered mixed stream was identical with that of the unfiltered mixed stream, but that introduced the addition step of filtration and a delay in the analysis.

The addition of alum to a pulp dispersion was thought to be controllable indirectly by the acidity of the mixed stream using a pH meter with a hydrogen-selective electrode, but the method took insufficient account of the accumulation of the sulphuric acid in the mill's recycled water and has been displaced by SCDs used off-line.

There is a need for an aggregation control method able to operate in-line on such aqueous dispersions as sewage, effluent, pulp dispersions and raw waters of all kinds.

One object of the invention is to provide such an in-line method and a device for employment in the method.

SUMMARY OF THE INVENTION

According to one aspect of the present invention there is provided a potentiometric method for sensing the charge of a mixed stream of an aggregant and an aqueous dispersion, suitable for use in an aggregation control loop process, which comprises flowing the mixed stream in contact with a metallic indicator electrode, measuring the potential difference between the indicator electrode and a second electrode of substantially stable potential different from that of the indicator electrode, whilst preventing any substantial electrical current from flowing between the electrodes.

For the purposes of this specification, aggregation means the process of coagulation, or that of flocculation.

Desirably the potential difference is measured with a device for measuring potential which allows only negligible electric current (e.g. less than $10^{-10}$ amps) to flow between the electrodes.

The second electrode may be a reference electrode, or (and preferably, when the mixed stream is earthed) an earthed electrode or an earthed connection to the reference terminal of the device for measuring potential.

It is common practice to classify electrodes as either metallic electrodes or membrane electrodes; a carbon electrode is classed as a metallic electrode.

The method may be carried out using a direct-reading pH meter or potentiometer equipped with the metallic indicator electrode. Such meters, hitherto, have been considered to respond solely to solute ions, their reactions and concentrations and are generally equipped with ion-specific membrane electrodes. No such electrochemical cell has been proposed for use in directly discriminating the reaction of an insoluble colloid with another oppositely charged colloid or colloidal solution. Earthing one electrode of a pH meter has never been proposed but surprisingly if such earthing is effected and an appropriate choice of indicator electrode is made, highly effective aggregant addition control of an earthed mixed stream can be achieved using such a pH meter.

There is no accepted theory which explains the present method. The inventors would not wish to be held to either of the following possible explanations, but is appears to them that the negatively charged surface of a cathode is a bite exerting electrostatic attraction on the free colloidal cationic aggregant which appears when the interaction of the colloids is substantially complete: there may follow a close association of the aggregant and the electrode surface, or a compression of the Helmholtz layer. Alternatively, an anionic aggregant (for example the copolyacrylic acids used in paper-making) may act as a ligand for metal ions released at the anode. Any such process would affect the potential of the electrode and the potential difference reading.

The interaction of an electrode surface and the aggregant will depend on the nature of the aggregant, the relative proportions of disperse phase and aggregant in the mixed stream, as well as on the electrode potential, electrode material, pH, temperature and flow rate. The latter three variables may be compensated, or so reduced in consequence that no compensation is required, for example when the aqueous dispersion is subject to pH, temperature or flow control.

Thus the method is directly sensitive to the charge condition of the mixed stream. No sensor, apart from SCDs, has been suggested for this use and none, including the SCDs, has been capable of in-line use in high solid streams such as sewage, effluent and pulp dispersions.

The indicator electrode should have no particular ion-specificity and a stable surface substantially chemically inert to the electrolytes in the mixed stream. Suitable metallic electrodes include stainless steel, gun metal bronze, carbon, gold, lead, platinum and silver, of which the first four have proven to be the most widely useful in the various mixed streams to which the method and device may be applied: the others are selectively useful, depending on the chemical nature of the stream. For example, lead and silver are changed at their surfaces by streams which contain hydrogen sulphide (sewage effluents) and platinum, from its sensitivity to hydrogen ion, is not preferred in streams with variable acidity.

Specifically excluded as indicator electrodes are membrane and ion-selective electrodes such as hydrogen electrodes used in pH measurement, where the response to a particular ion is dominant and obscures whatever response such as electrode may have to the charge condition of the stream.

According to a further aspect of the invention a device for sensing the course of the aggregation of an aqueous dispersion of charged particles in an aggregation control loop process, comprises a galvanic cell having a metallic indicator electrode without any particular ion-specificity and a second electrode, the electrolyte of the cell being a mixed stream of the dispersion and an aggregant for the charged particles and being in contact with the indicator electrode, and a means for sensing the potential difference appearing between the electrodes.

The potential difference of the galvanic cell may arise spontaneously from the difference in the potentials of the two electrodes, or the potential difference may be impressed on the cell by an external source of stable e.m.f. bridging the electrodes. In the latter case the electrodes may be of similar composition.

In a cell with an impressed potential difference, preferably both electrodes are metallic.

In a cell in which the potential difference arises spontaneously, the second electrode acts as a reference electrode developing a substantially stable potential so that the changes in the potential of the indicator electrode may be recognised by changes in the cell e.m.f.. The known reference electrodes comprising half cells of a metallic electrode in a standard solution, for example the silver/silver chloride(solid)/KCal (solution) composite are useful, as are a silver/silver chloride solid electrode with no surrounding standard solution, and, particularly for use in the aggregation of particles in effluent and sewage, a silver/silver sulphide electrode.

Whilst the indicator electrode must contact the mixed stream, it is not always necessary that the second electrode should do so. If there is no extraneous, significant, variable electrical field, such as would form a ground loop affecting the potential difference, and the mixed stream is earthed, it is sufficient that the second electrode is an earthed connection from the voltmeter directly to earth or to a metal conduit carrying the stream. Preferably such earthed connection is the anode.

The indicator electrode or both electrodes may be housed in a conduit which determines the path of the mixed stream, or they may be mounted externally on a body for immersion in the mixed stream.

The potential difference is desirably measured by a high impedance voltmeter drawing insufficient electric current to affect the potential difference between the electrodes—available electronic voltmeters operating with a current of from $10^{-12}$ to $10^{-14}$ amperes are ideal, preferably the voltmeter incorporates electronic amplification to produce a signal which can be displayed in a digital and/or analog form. The conductivity of the mixed stream is of no consequence to the operation of a sensor cell comprising such a voltmeter.

There is, in the vicinity of aggregation, for each substantial change in the electrical double layers of the particles, a corresponding and substantially unique potential difference which is sensed by the method and device of this invention. If there is efficient aggregation of the particles, the corresponding measured potential difference can be used as a datum signal for the preservation of that condition despite changes in the concentration of particles and/or the charges they carry.

Furthermore, the indicator electrode may be situated no more than 30 seconds in real time downstream of an aggregant dosing point: this short response time is valuable to close control and compares with 40 minutes real time delay for a jar test and 5 to 8 minutes delay for an SCD operating on a filtrate derived from the stream.

It should be understood that a control loop method based on the method of the invention does not determine the best coagulation conditions, but will preserve a selected coagulation condition established by other means by preserving the datum signal generated by the selected condition.

The method of the invention may discriminate the effect of a trace, say less than 1 part per million, of coagulants such as hydroxylic polymers of aluminium and of ferric iron in the vicinity of efficient coagulation, and flocculants such as synthetic polycations. The method may also, in similar circumstances, discriminate traces of polyanionic substances, for example copolyacrylic acids and polyphosphates, used in paper-making.

When it is intended that the indicator electrode and a reference electrode both contact the mixed stream, the electrodes may be disposed relatively to each other transversely or longitudinally of the path of the stream.

A range of useful datum potential differences is available from the choices of cell conformations, electrode materials and/or externally applied e.m.f..

Monitoring aqueous streams in conduits from capillaries to pipes of several hundred millimeters diameter would encompass most practical applications, but no limit has been found on the size of the conduit or the rate of flow of the liquid.

In dealing with some mixed streams, it is seldom possible to use a sampling pump to abstract a side stream from the very large works' pipes (frequently 700 mm diameter) to feed to the sensor cell, firstly because such mixed streams are prone to block the pump and secondly such fast acting pumps wear quickly from contact with the abrasive material such mixed streams frequently contain. In these circumstances and the absence of interfering ground loops, the indicator electrode may be let into the pipe (electrically insulated from the pipe if it is metallic) and the second electrode may be a connection between the voltmeter and earth or to the pipe as appropriate.

The surface of an electrode in contact with some mixed streams, will be kept in working condition by abrasion from components in the mixed stream. In other cases the surface may become fouled and then must be cleaned by mechanical abrasion, electrolytically, or ultrasonically. The or each electrode may be placed or shaped to reduce the incidence

5 of fouling—flush fitting in the inner wall of the conduit, cambering, or streamlining.

BRIEF DESCRIPTION OF THE DRAWINGS

The invention will now be further described, by way of example, with reference to the accompanying drawings, in which.

DESCRIPTION OF PREFERRED EMBODIMENTS

Figure 1:
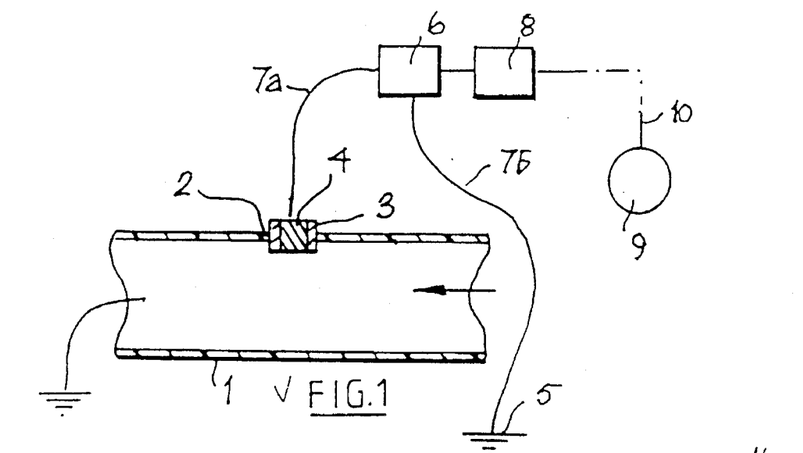
FIGS. 1 to 5 are schematic cross-sectional representations of a series of devices according to the invention showing variations in a measuring cell.

Referring to FIG. 1, a length of horizontal works' pipe 1 (through which flows the grounded works' effluent) shown sectioned on a vertical diameter, has a port 2 closed by an insulating rubber collar 3 surrounding a silver indicator electrode 4. An earthed connection 5 serves as a reference electrode. The electrodes 4 and 5 are bridged by a high impedance voltameter 6 via screened cables 7a and 7b respectively. The output of the voltameter is connected to a signal processor 8 from which a control signal is relayed to a chemical dosing pump 9 via a control line 10.

Apparatus according to FIG. 1 was installed at an effluent works using a commercial polyquaternaryammonium salt as flocculant. The works' chemist established the dose of flocculant to give satisfactory flocculation and the datum reading of the voltameter 6 was established as 97. The control loop was put in control of the flocculant dosing pump 9 to preserve a datum reading of 97 and through three weeks of continuous operation, the quality of flocculation remained constant without need of recalibration of the datum reading. During a period of about two hours, the dispersion was of low solids content and the dosing pump stalled under the low revolutions demanded by the automatic control. Manual control was instituted to maintain the datum reading. The quality of the flocculation continued satisfactory and was later returned to automatic control. Over the three week period a 25% saving of flocculant was logged and the plant had not previously enjoyed such a sustained period of acceptable flocculation.

Figure 2:
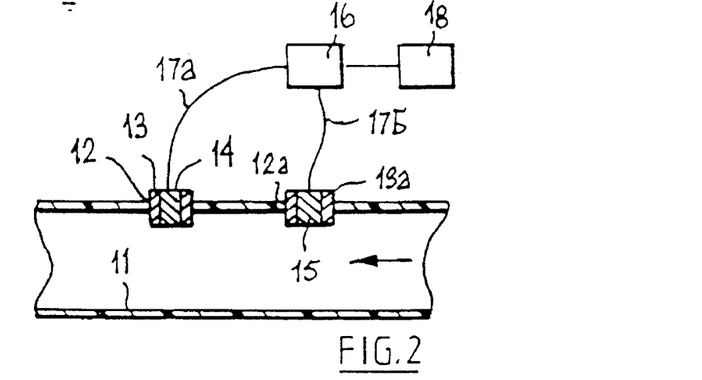

Referring to FIG. 2, a polypropylene pipe 11 shown in longitudinal vertical cross-section, conducts an ungrounded mixed stream. A port 12 in the pipe is sealed by a collar 13 of synthetic rubber surrounding a stainless steel indicator electrode 14. A reference electrode 15 of silver/silver sulphide is housed within an insulating collar 13a sealing port 12a. The electrodes 14 and 15 are bridged by a high impedance voltameter 16 via screened cables 17a and 17b and the output of the voltmeter is connected to a signal processor 18. The processor 18 is used to control the addition of aggregant to the stream flowing in pipe 11 upstream of the region shown.

Figure 3:
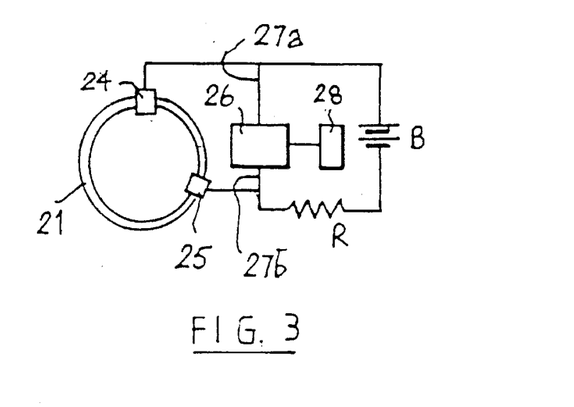

Referring to FIG. 3, a right-sectioned cylindrical conduit 21, of polyvinyl chloride, shown end-on, has a screwed-in indicator electrode 24 and a reference electrode 25, both of stainless steel. The electrodes are bridged firstly by a high impedance voltmeter 26 through cables 27a and 27b, and secondly by a battery B having an e.m.f. of 2 volts connected in series with a resistor R of 0.4 megohms. The voltmeter 26 is connected to a signal processor 28. The processor 28 is used to control the addition of aggregant to the stream flowing in pipe 21.

Figure 4:
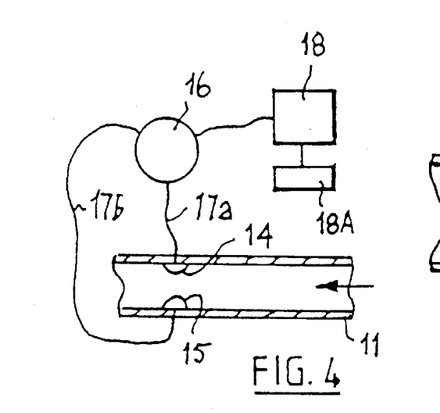

FIG. 4 shows an alternative arrangement to FIG. 2, the electrodes 14 and 15 being opposite each other and differently mounted in the tube.

Figure 5:
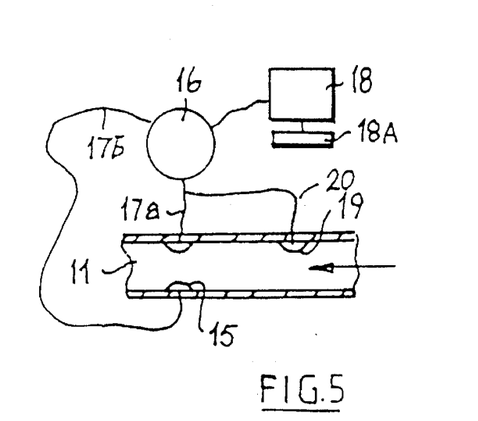

Referring to FIG. 5, the numbered items 11 to 18 have the meaning given to items 11 to 18 in FIG. 4, but an additional electrode 19 is set upstream of the other electrodes and a screened cable 20 connects electrodes 14 and 19. The third electrode 19 increased the potential difference available from the cell and ay make amplifying of the output signal unnecessary.

Figure 7:
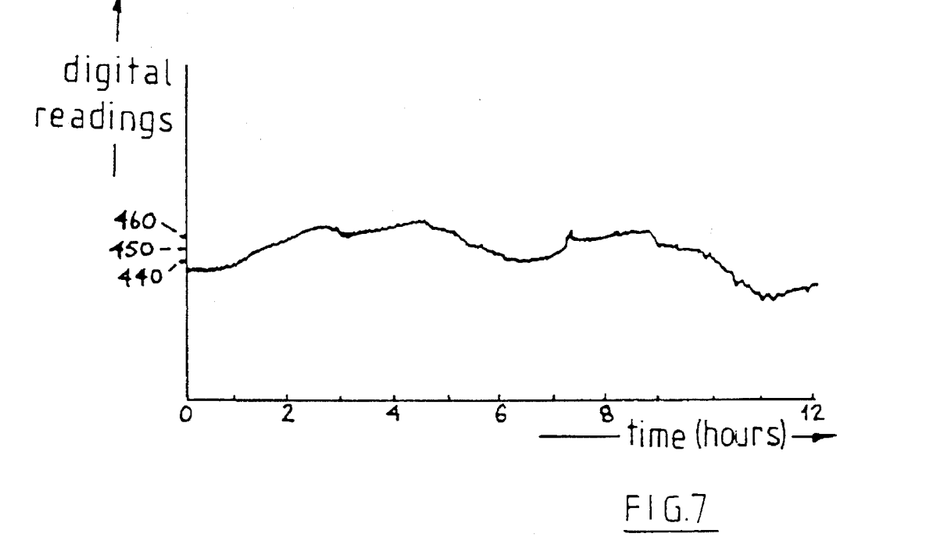
FIG. 7 is a reproduction of a chart recording of an inefficiently coagulated effluent stream monitored by a device according to the invention.
Figure 8:
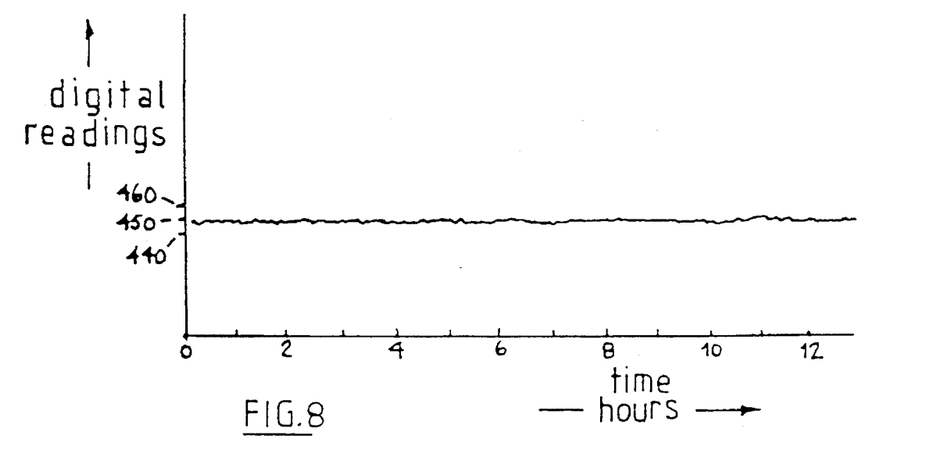
FIG. 8 is a reproduction of a chart recording of an effluent stream dosed in accordance with the output of a device according to the invention.

In a trial at a slaughterhouse, unfiltered effluent from the slaughterhouse was flowed through the conduit 11 of FIG. 5 (diameter 5 centimeters) and the characteristic reading was exhibited on a digital display 18A. FIG. 7 shows the record of the display over a twelve hour period with dosing of a suitable coagulant determined under manual control guided by jar tests. During this period the coagulation was more often poor than good. FIG. 8 shows the record of continuous manual adjustment of the coagulant dose guided by the digital display 18A. Good coagulation was known to occur at a reading of 450 and the dosing adjustments were undertaken to seek to maintain this figure. The coagulation was of consistently good quality throughout this period and it was found that there was a display band width of from 443 to 455 in which this quality was assured. This performance would be guaranteed if the output signal of the processor 18 was used to control coagulant dosing in a coagulant dose control loop.

Figure 6:
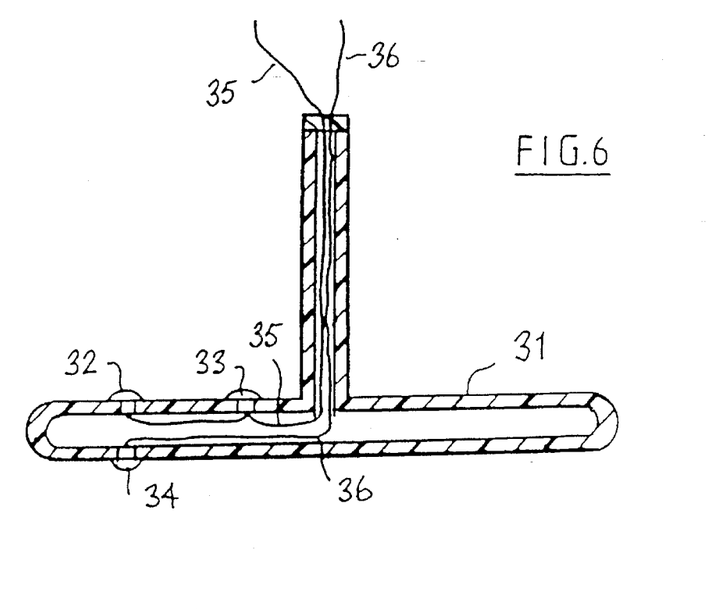
FIG. 6 is a cross-sectional representation of a cell with external electrodes.

Referring to FIG. 6, a portable cell for use in the method of the present invention comprises a T-piece 31 of polyvinyl chloride which carries external electrodes 32, 33 and 34 of M316 stainless steel. Electrodes 32 and 33 are connected by screened cable 35 and electrode 34 is connected to a cable 36. Cables 35 and 36 issue from the T-piece 31 for connection of a high impedance amplifier and signal processor (not shown). This form of device is useful for occasional or permanent examinations of industrial effluent streams running in otherwise inaccessible gullies. The device of FIG. 6 has been tested successfully in a gully 3.7 meters deep in which ran effluent from a paper mill. This effluent had routinely blocked a sampling pump meant to lift a continuous sample to the filter of a filter/SCD sensing device used for monitoring a parameter of the effluent. The cell shown in FIG. 6 enabled effective parameter monitoring to be achieved without blockage problems.

Figure 9:
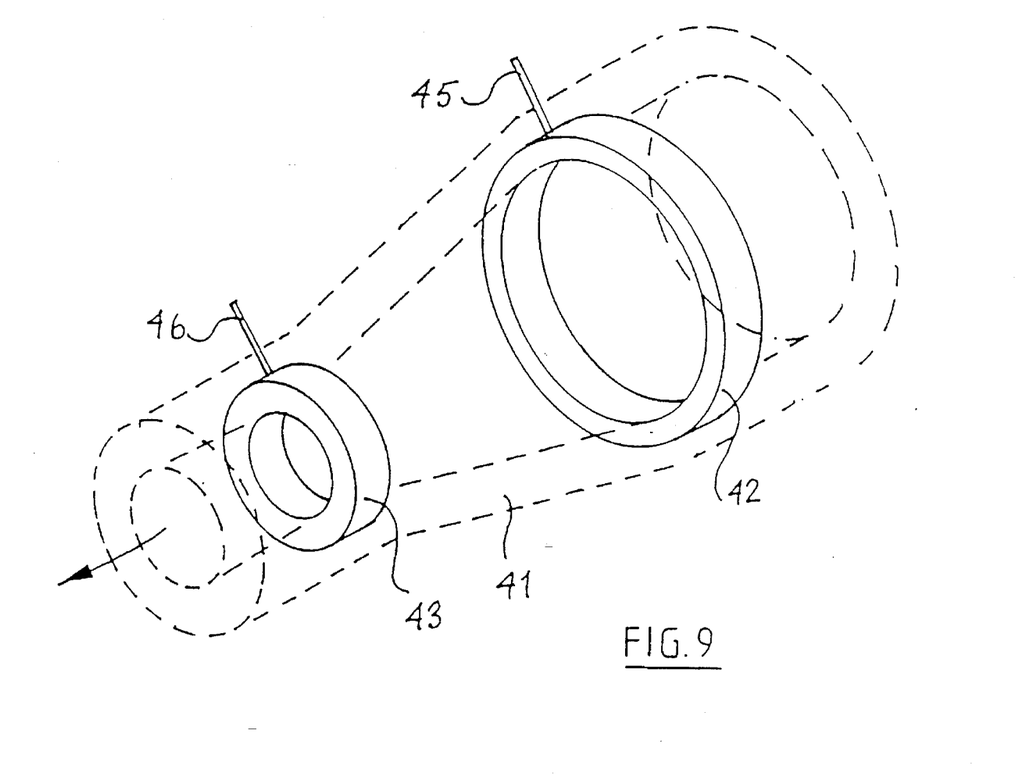
FIGS. 9 and 10 show alternative arrangements of electrodes in sensing devices according to the invention.

Referring to FIG. 9, a conduit 41 of partial frusto-conical shape is shown, housing a larger annular electrode 42 having an internal diameter of 12.5 millimeters, at the wide end of the frusto-conical part and a smaller annular electrode 43 having an internal diameter of 6.25 millimeters at the narrow end; each of the electrodes 42 and 43 is equipped with an extension 45 or 46 respectively, which penetrates the wall of the conduit for electrical connection to a voltmeter (not shown).

An advantage of a venturi-shaped zone with the electrodes situated at the narrowest bore is that there is a self-cleaning effect achieved with this set-up caused by the acceleration of flow of the liquid as it streams through the constricted bore.

Figure 10:
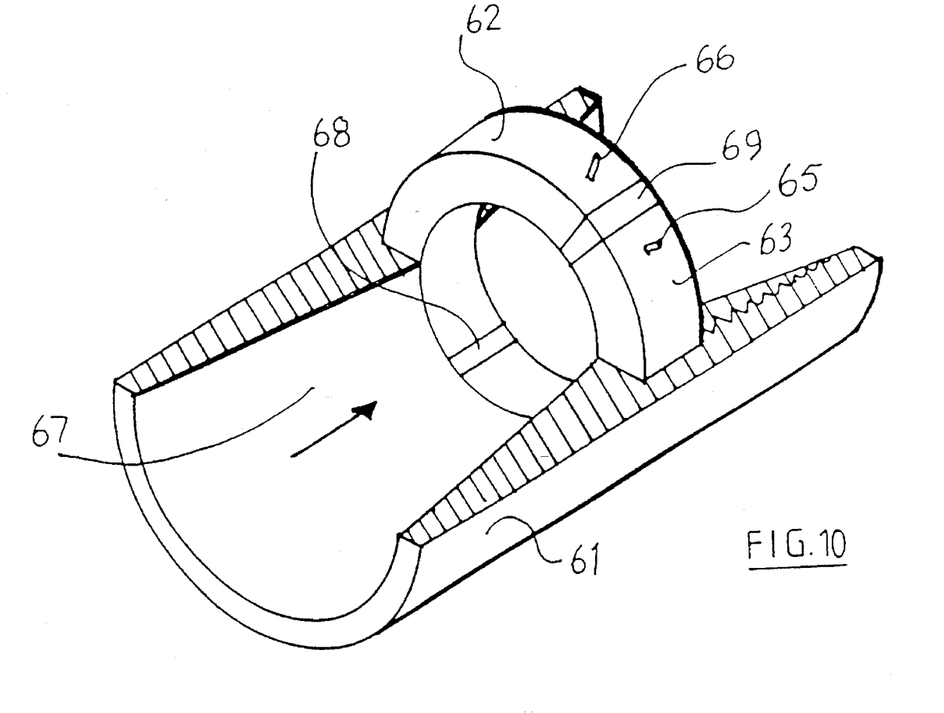

Referring to FIG. 10, a conduit 61 of polypropylene has a waisted bore 67 and houses stainless steel electrodes 62 and 63 with non-conducting spacers 68 and 69 all located at the waist, flush with the boundary of the bore. Stainless steel lugs 65 and 66 are secured to the electrodes 63 and 62 respectively for connection to other elements of the cell.

Figure 11:
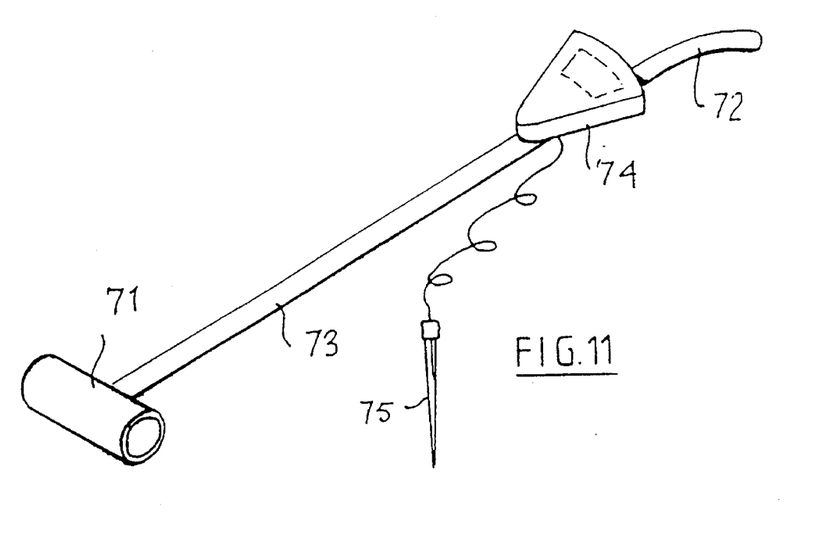
FIG. 11 shows a portable cell for use in the method of the invention.

FIG. 11 shows a modified form of portable test device for use in the method of the invention. Hollow tube 71 includes an electrode pair (e.g. such as shown in FIG. 10) which can be dipped into a flowing stream using handle 72 and hollow support shaft 73. The potential created across the electrode pair is sensed by a millivoltmeter 74 via wires passing through the hollow shaft 73. An earthing spike 75 can be clipped to the shaft 73 when not required, but is used to ground one side of the voltmeter if a grounded effluent stream is being monitored, in which case only the indicator electrode (62) need be connected to the other side of the voltmeter.

We claim:

1. A method for sensing the course of an aggregation of an aqueous dispersion of charged particles in an aggregation control loop comprising a galvanic cell having a metallic indicator electrode without any particular ion-specificity and a second electrode, the electrolyte of the cell being a mixed stream of the dispersion and an aggregant for the charged particles, adding the aggregant to the stream upstream of the electrodes and mixing the aggregant into the stream to form the mixed stream, maintaining the electrolyte in contact with the indicator electrode, sensing a potential difference appearing between the electrodes, and controlling the addition of the aggregant to maintain the potential difference within a control range.

2. A method as claimed in claim 1, in which the second electrode is a reference electrode.

3. A method as claimed in claim 1, in which the second electrode is connected to earth.

4. A method as claimed in claim 1, in which the mixed stream is caused to flow in a conduit, and the electrodes are located in the conduit.

5. A method as claimed in claim 1, in which the electrodes are located on a body, and the body is immersed in the stream.

6. A method for monitoring an aggregation control loop process comprising the steps of:

(a) providing a stream of an aqueous dispersion of charged particles;

(b) dosing the stream of the aqueous dispersion of charged particles with an aggregant to produce a mixed stream;

(c) providing a reference electrode at a selected location having a stable electrical potential;

(d) locating an indicator electrode in contact with the mixed stream to measure an electrical potential generated by the mixed stream at the indicator electrode; and (e) monitoring the electrical potential between the indicator electrode and the reference electrode to establish a selected electrical potential for the mixed stream.

7. The method according to claim 6 comprising the step of locating the reference electrode in the mixed stream.

8. The method according to claim 6 comprising the steps of providing a conductive pipe for directing the mixed stream along a selected path and locating the reference electrode in contact with earth.

9. The method according to claim 6 wherein the monitoring step is effected by providing a voltmeter that permits only a minimal flow of current to measure the electrical potential between the indicator electrode and the reference electrode.

10. The method according to claim 9 comprising the step of monitoring the mixed stream using the voltmeter to detect fluctuations in the electrical potential between the indicator electrode and the reference electrode from the selected electrical potential.

11. The method according to claim 10 comprising the step of adjusting the dosing of the aqueous dispersion of charged particles with the aggregant upon detection of fluctuations in the electrical potential so that the electrical potential between the indicator electrode and the reference electrode returns to the selected electrical potential.

12. An apparatus for monitoring a mixed stream flowing in a conduit comprising:

(a) control means positioned along the conduit for dosing an aqueous dispersion of insoluble charged particles flowing in the conduit with an aggregant thereby forming the mixed stream; and (b) a potentiometer for positioning along the conduit downstream of said control means, said potentiometer having a metal indicator electrode and a reference electrode for electrical contact with the mixed stream, said potentiometer providing a measurement of an electrical potential of the mixed stream, said control means being responsive to said measurement to maintain the electrical potential of the mixed stream at a selected level by regulating the dosing effected by said control means.

13. The apparatus as recited in claim 12 comprising a signal processor responsive to said potentiometer for regulating the dosing by said control means so that the electrical potential of the mixed stream is automatically maintained at the selected level.

14. The apparatus as recited in claim 12 wherein the conduit has a port downstream of the control means, said indicator electrode being mounted in the port, said apparatus comprising an insulating collar encircling said indicator electrode for insulating said indicator electrode from the conduit and for protecting said indicator electrode from damage by the mixed stream.

15. The apparatus as recited in claim 12 wherein the conduit has an annular housing downstream of said control means, said indicator electrode being annular in shape and dimensioned to engage within the housing of the conduit.

16. The apparatus as recited in claim 12 wherein the conduit is electrically connected to earth and wherein said reference electrode of said potentiometer is electrically connected to earth.

17. An apparatus for monitoring a flowing mixed stream comprising:

(a) an earthed conduit for directing the mixed stream along a selected path;

(b) control means positioned along said conduit for dosing an aqueous dispersion of insoluble charged particles flowing in said conduit with an aggregant thereby forming the mixed stream;

(c) a potentiometer having a metal indicator electrode positioned within said conduit downstream of said control means for contacting the mixed stream, said indicator electrode having a charged outer surface of like polarity as the charged particles so that the charged particles in the dispersion are repelled away from said indicator electrode, said potentiometer also having a reference electrode for electrically connecting to earth, said potentiometer providing a measurement of an electrical potential between the mixed stream and earth; and (d) a signal processor responsive to said potentiometer for regulating the dosing of said control means so that the electrical potential of the mixed stream is automatically maintained within a selected range.

18. The apparatus as recited in claim 17 wherein said conduit includes an interior frustoconical surface to accelerate the flow of the mixed stream and wherein said indicator electrode is positioned in the accelerated flow to allow cleaning of said indicator electrode.

19. The apparatus as recited in claim 17 wherein said conduit includes a waisted bore, said indicator electrode being annular in shape and positioned in said waisted bore of said conduit.

\* \* \* \* \*

UNITED STATES PATENT AND TRADEMARK OFFICE
CERTIFICATE OF CORRECTION

PATENT NO. : 5,485,099
DATED : January 16, 1996
INVENTOR(S) : Brian Collins and Michael J. Blanchard It is certified that error appears in the above-indentified patent and that said Letters Patent is hereby corrected as shown below:

Column 1, line 22, "change" should be --charge--;

Column 1, line 32, "jaw" should be --jar--;

Column 2, line 47, "bite" should be --site--;

Column 6, line 22, "ay" should be --may--.

Signed and Sealed this

Fourteenth Day of May, 1996

Attest:

BRUCE LEHMAN

*Attesting Officer*    *Commissioner of Patents and Trademarks*